US011749405B2

(12) United States Patent
Stewart et al.

(10) Patent No.: US 11,749,405 B2
(45) Date of Patent: Sep. 5, 2023

(54) SYSTEMS AND METHODS FOR DYNAMIC BIOMETRIC DETECTION AND RESPONSE

(71) Applicants: Robin H. Stewart, Woodbridge, VA (US); Qiliang Li, Fairfax, VA (US)

(72) Inventors: Robin H. Stewart, Woodbridge, VA (US); Qiliang Li, Fairfax, VA (US)

( * ) Notice: Subject to any disclaimer, the term of this patent is extended or adjusted under 35 U.S.C. 154(b) by 489 days.

(21) Appl. No.: 16/928,464

(22) Filed: Jul. 14, 2020

(65) Prior Publication Data

US 2021/0052170 A1 Feb. 25, 2021

Related U.S. Application Data

(60) Provisional application No. 62/922,623, filed on Aug. 20, 2019, provisional application No. 62/973,470, filed on Oct. 7, 2019.

(51) Int. Cl.
*G16H 50/20* (2018.01)
*A61B 5/0205* (2006.01)
(Continued)

(52) U.S. Cl.
CPC .......... *G16H 50/20* (2018.01); *A61B 5/0022* (2013.01); *A61B 5/02055* (2013.01); *A61B 5/1112* (2013.01); *A61B 5/1117* (2013.01); *A61B 5/14532* (2013.01); *A61B 5/14551* (2013.01); *A61B 5/681* (2013.01); *A61B 5/7264* (2013.01); *A61B 5/746* (2013.01); *A61J 7/0427* (2015.05); *G06F 18/2132* (2023.01); *G06F 18/2135* (2023.01); *G16H 10/60* (2018.01); *G16H 50/30* (2018.01); *A61B 2562/0219* (2013.01); *A61J 2205/60* (2013.01)

(58) Field of Classification Search
CPC .. G06K 9/00496; G06K 9/6284; G16H 10/60; G16H 50/30; G16H 50/20; G16H 80/00
See application file for complete search history.

(56) References Cited

U.S. PATENT DOCUMENTS 9,159,223 B2 * 10/2015 Proud .................... A61B 5/681
2016/0012249 A1 * 1/2016 Keppler ............... G06F 16/955
726/28

(Continued)

*Primary Examiner* — Mark Holcomb
(74) *Attorney, Agent, or Firm* — April M. Mosby; Monarch IP Group, PLLC

(57) ABSTRACT

Systems and methods of dynamic biometric detection and response are provided for the purpose of establishing baseline health status while conveying real-time drug prescription usages and reactions from baseline data. The dynamic monitoring system may be embedded within a wristband, ring, vest, and/or waistband in wireless communication with a computing device or server. Each wearable device may employ interchangeable and embedded sensors to detect inertia movements; 360-imaging fall detections; and a variety of body-emitting vital signs. The system may include a processor operable to sense user location, motion, activity, and biomarkers for the purpose of detecting the user's behavior pattern, wherein an enhanced machine-learning algorithm is used to identify repetitive actions within the user's behavior pattern; and, based upon this pattern, the system is able to detect one or more anomalies for the purpose of generating an anomaly alert for third party notification and quantitative analysis at a server.

16 Claims, 8 Drawing Sheets

(51) Int. Cl.
  *A61B 5/00*     (2006.01)
  *A61B 5/11*     (2006.01)
  *A61B 5/145*    (2006.01)
  *A61B 5/1455*   (2006.01)
  *A61J 7/04*     (2006.01)
  *G16H 10/60*    (2018.01)
  *G16H 50/30*    (2018.01)
  *G06F 18/2132*  (2023.01)
  *G06F 18/2135*  (2023.01)

(56) References Cited

U.S. PATENT DOCUMENTS

| | | | |
|---|---|---|---|
| 2019/0209022 A1* | 7/2019 | Sobol | A61B 5/0022 |
| 2020/0085300 A1* | 3/2020 | Kwatra | G16H 20/00 |
| 2020/0222284 A1* | 7/2020 | Musini | G16H 40/63 |

* cited by examiner

SYSTEMS AND METHODS FOR DYNAMIC BIOMETRIC DETECTION AND RESPONSE

CROSS REFERENCE TO RELATED APPLICATIONS

This present application relates to commonly-owned U.S. patent application Ser. No. 62/922,623, entitled "Wireless Communicating, Detecting, Conveyance, Technology Bands," naming Robin Hardie Stewart and Qiliang Li as the inventors, filed Aug. 20, 2019, which is the application from which the present application is entitled to the benefit of the filing date; the contents of which are incorporated by herein by reference in its entirety. Additionally, the present application relates to commonly-owned U.S. Patent Application Ser. No. 62/973,470, entitled "Wireless Prescription and medical communicating band," naming Robin Hardie Stewart and Qiliang Li as the inventors, filed Oct. 21, 2019; which is also a application from which the present application is entitled to the benefit of the filing date, the contents of which are incorporated by herein by reference in its entirety.

BACKGROUND

Patients often need ongoing monitoring of heartbeat, blood pressure, blood glucose, and various other medical statistics. Most physicians rely upon stand-alone equipment to monitor their patients. These differing types of medical equipment are typically bulky, heavy machines in excess of fifty pounds that sit along side a hospital bed or within a physician's office, requiring additional staff to install and monitor. As a consequence, these systems can be quite costly when considering the equipment expense, training, and staff necessary to operate. Although these types of equipment are effective, these systems are temporary in that the patient can only be monitored at the doctor's office or a hospital. There is no on-going monitoring that occurs with the use of these systems. Further, although most of the medical monitoring used in hospitals and at physician's offices can be effective, they typically only measure one biometric variable per machine.

Portable professional health monitoring models do exist that a physician can rely upon. Yet, these models are quite bulky and not for general wear. In particular, a user is inhibited from walking around and performing their normal daily activities. Specifically, most of these portable models must be plugged into a power socket and most possess numerous wires that make it complicated and unflattering to wear under or over most types of clothing, while being monitored.

Consumer medical monitoring devices are available. Some of these consumer products can be worn wirelessly. Yet, most of these devices are not manufactured using the same level of quality standards that are applied to ordinary professional hospital equipment. Thereby, the data acquired by these devices are not reliable enough for the medical community.

It is within this context that the embodiments arise.

SUMMARY

Embodiments of a system and method for dynamic biometric detection and response are provided. It should be appreciated that the present embodiment can be implemented in numerous ways, such as a process, an apparatus, a system, a device, or a method. Several inventive embodiments are described below.

In some embodiments, a system and method for dynamic biometric detection and response is provided. As an initialization process, the method may include initializing a safety and security protocol. Further, the method may include retrieving a user profile from a storage unit. The method may also include identifying user location and sensing user motion. In particular, the data processing method may include the step of sensing one or more satellite signals within the Global Positioning System (GPS), to detect the travel time of the signal; to calculate the distance between the system and at least one satellite; and to calculate the user location based upon this distance. Sensing user motion may occur by retrieval of at least one of the user's specific force, angular rate, or orientation from an Inertial Measurement Unit (IMU). The method may further include detecting user activity based upon the sensed user motion, the detected location, and the user profile. In particular, the system may include a data processing step of parsing the user profile to identify a predetermined set of locations and associated activities, wherein each activity includes a corresponding motion. From a comparison of the detected location with the predetermined set of locations, the method may include comparing the sensed user motion with the corresponding motion of the matched location to identify the user's location. Further, the method may include sensing the biomarkers of the user and detecting the user's behavior pattern. In particular, the system may include the step of retrieving the user's temperature from a thermometer; retrieving the user's blood pressure from a sensing unit having a deep learning algorithm associated with monitoring heart rate; retrieving the user's blood oxygen level from a pulse oximeter blood oxygen sensor; retrieving the user's blood glucose level from a non-invasive glucose monitor; and/or retrieving the user's pulse from an optical heart sensor. Further, the method may include detecting the user's behavior pattern. For example, the method may include monitoring user activity using advanced machine-learning algorithms, including principal component analysis and neural network computations; and identifying repetitive actions to indicate the detected user behavior pattern. Moreover, the method may include detecting an anomaly based upon the detected user's behavior pattern, the sensed biomarkers, the user activity, and the user profile; and generating an anomaly alert for third party notification and quantitative analysis at a server.

In some embodiments, a monitoring system having dynamic biometric detection and response is provided. The monitoring system may include a processor coupled to a memory; wherein the processor is operable to initialize a safety and security protocol. The processor may also be operable to retrieve a user profile from a storage unit, identify user location, and sense user motion. In particular, the processor may be able to sense one or more satellite signals within the GPS, detect the travel time of the signal, calculate the distance between the processor and at least one satellite, and calculate the user location based upon this distance. Sensing user motion may occur by retrieval of at least one of the user's specific force, angular rate, or orientation from an IMU. The processor may be further operable to detect user activity based upon the sensed user motion, the detected location, and the user profile. In particular, the processor may be able to parse the user profile to identify a predetermined set of locations, and associated activities, wherein each activity includes a corresponding motion. From a comparison of the detected location with the predetermined set of locations, the processor can compare the sensed user motion with the corresponding motion of the matched location. Further, the processor may be operable to sense biomarkers of user and detect user behavior pattern. For example, in some embodiments the processor may retrieve one or more to the following: the user's temperature from a thermometer, the user's blood pressure from a sensing unit having a deep learning algorithm associated with monitoring heart rate, the user's blood oxygen level from a pulse oximeter blood oxygen sensor, the user's blood glucose level from a non-invasive glucose monitor, and/or the user's pulse from an optical heart sensor. Further, the method may include detecting the user's behavior pattern. For example, the method may include monitoring user activity using advanced machine-learning algorithms, including principal component analysis and/or neural network computations; and identifying repetitive actions to indicate the detected user behavior pattern. Moreover, the processor may be operable to detect an anomaly based upon the detected user behavior pattern, the sensed biomarkers, user activity, and the user profile and generate an anomaly alert for third party notification and quantitative analysis at a server.

In some embodiments, a tangible, non-transitory, computer-readable media having instructions whereupon which, when executed by a processor, cause the processor to perform the dynamic biometric detection and response method described herein. The method may include retrieving a user profile from a storage unit. The method may further include identifying user location and sensing user motion. In particular, the method may include the step of sensing one or more satellite signals within the GPS, to detect the travel time of the signal; to calculate the distance between a processor and at least one satellite; and to calculate the user location based upon this distance. Sensing user motion may occur by retrieval of at least one of the user's specific force, angular rate, or orientation from an IMU. The method may further include detecting user activity based upon the sensed user motion, the detected location, and the user profile. In particular, the method may include the data processing step of parsing the user profile to identify a predetermined set of locations and associated activities, wherein each activity having a corresponding motion. From a comparison of the detected location with the predetermined set of locations, the method may include comparing the sensed user motion with the corresponding motion of the matched location to identify the user's location. Further, the method may include sensing the biomarkers of user and detecting user behavior pattern. In particular, the method may include the step of retrieving the user's temperature from a thermometer; retrieving the user's blood pressure from a sensing unit having a deep learning algorithm associated with monitoring heart rate; retrieving the user's blood oxygen level from a pulse oximeter blood oxygen sensor; retrieving the user's blood glucose level from a non-invasive glucose monitor; and/or retrieving the user's pulse from an optical heart sensor. Further, the method may include detecting the user's behavior pattern. For example, the method may include monitoring user activity using advanced machine-learning algorithms, including principal component analysis and neural network computations; and identifying repetitive actions to indicate the detected user behavior pattern. Moreover, the method may include detecting an anomaly based upon the detected use's behavior pattern, the sensed biomarkers, the user activity, and the user profile; and generating an anomaly alert for third party notification and quantitative analysis at a server.

Other aspects and advantages of the embodiments will become apparent from the following detailed description taken in conjunction with the accompanying drawings which illustrate, by way of example, the principles of the described embodiments.

BRIEF DESCRIPTION OF THE DRAWINGS

The described embodiments and the advantages thereof may best be understood by reference to the following description taken in conjunction with the accompanying drawings. These drawings in no way limit any changes in form and detail that may be made to the described embodiments by one so skilled in the art without departing from the spirit and scope of the described embodiments.

DETAILED DESCRIPTION

Figure 1:
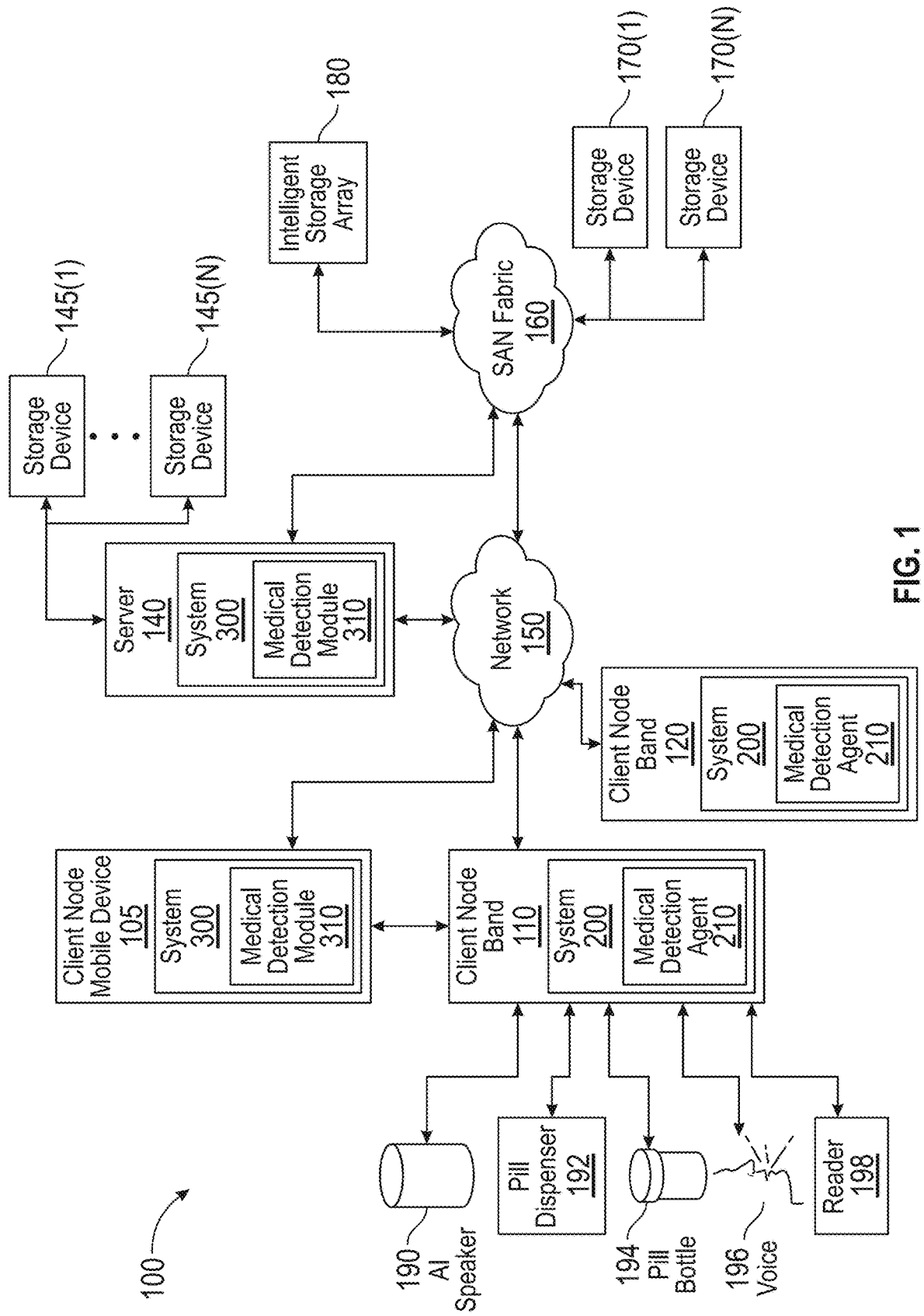
FIG. 1 is a system diagram of an exemplary network incorporating the systems and methods of dynamic biometric detection and response, in accordance with some embodiments.

The following embodiments describe a system and method for dynamic biometric detection and response. It can be appreciated by one skilled in the art, that the embodiments may be practiced without some or all of these specific details. In other instances, well known process operations have not been described in detail in order not to unnecessarily obscure the embodiments.

Systems and methods of dynamic biometric detection and response are provided herein for the purpose of establishing baseline health status while conveying real-time drug prescription usages and reactions from baseline data. The dynamic monitoring system described herein may be embedded within a wristband, ring, vest, and/or waistband in wireless communication with a computing device, a server, and the like. Each interoperable device may employ an array of biometric and telemetric sensors. These sensors can be interchangeable and embedded sensors that detect inertia movements; 360-imaging fall detections; and body-emitting vital signs (including but not limited to heart rate, temperature, blood oxygen, blood pressure, blood glucose level). Whether in an active living community or hospice, the system and method for dynamic biometric detection and response can provide physical mobility, physical strength, and other biomarker alerts in real-time with accuracy. In particular, the system may include a processor operable to sense user location, motion, activity, and biomarkers for the purpose of detecting the user's behavior pattern, wherein an enhanced machine-learning algorithm is used to identify repetitive actions within the user's behavior pattern; and, based upon this pattern, to detect one or more anomalies. Further, the system can generate an anomaly alert for third party notification and quantitative analysis at server can be generated.

In some embodiments, a system and method for dynamic biometric detection and response may include a processor coupled to a memory; wherein the processor is operable to retrieve a user profile from a storage unit, identify user location, and sense user motion. For example, in some embodiments the processor may be able to sense one or more satellite signals within the GPS, detect the travel time of the signal, calculate the distance between the processor and at least one satellite, and calculate the user location based upon this distance. Sensing user motion may occur by retrieval of at least one of the user's specific force, angular rate, or orientation from an IMU. The processor may be further operable to detect user activity based upon the sensed user motion, the detected location, and the user profile. For example, in some embodiments the processor may be able to parse the user profile to identify a predetermined set of locations, and associated activities, wherein each activity includes a corresponding motion. From a comparison of the detected location with the predetermined set of locations, the processor can compare the sensed user motion with the corresponding motion of the matched location in an effort to identify the activity of the user. Further, the processor may be operable to sense biomarkers of user and detect user behavior pattern. For example, in some embodiments the processor may retrieve one or more to the following: the user's temperature from a thermometer, the user's blood pressure from a sensing unit having a deep learning algorithm associated with monitoring heart rate, the user's blood oxygen level from a pulse oximeter blood oxygen sensor, the user's blood glucose level from a non-invasive glucose monitor, and/or the user's pulse from an optical heart sensor. These sensors can be interchangeable and embedded within a band having the system and method described herein. Further, the method may include detecting the user's behavior pattern. For example, the method may include monitoring the user action using advanced machine-learning algorithms, including principal component analysis and neural network computations; and identifying repetitive actions to indicate the detected user behavior pattern. Moreover, the processor may be operable to detect an anomaly based upon the detected user behavior pattern, the sensed biomarkers, user activity, and the user profile and generate an anomaly alert for third party notification and quantitative/qualitative data analysis and reporting at a server.

In some embodiments, the processor may detect the user behavior pattern by monitoring user activity and motion using advanced machine-learning algorithms, including principal component analysis and neural network computations. From the detected activities or motions, the processor may be able to identify repetitive actions and motions that indicate the detected user behavior pattern. The system may be embedded in a wearable band to provide a variety of health monitoring biomarkers and physical assessments to a third party computing device. These biomarkers can range from measuring an individual's athletic ability to detecting a user fall.

In some embodiments, the processor may detect an anomaly associated with a user by retrieving the detected user behavior pattern, the sensed biomarkers, user activity, and the user profile. Further, the processor may be operable to parsing the user profile to identify a stored user behavior pattern. In particular, the processor may compare the user activity with the detected user behavior pattern and the stored user behavior pattern in an effort to detect a match. When no match is found, the processor may generate in response an anomaly alert and update the user profile with the anomaly alert. Further, the processor may be operable to generate a report based upon the anomaly alert and send the report to an interested third party, such as a relative or physician. The report may be sent to a server for qualitative data analysis and reporting based upon user profile.

In some embodiments, the processor may be operable to trigger a Radio-Frequency Identification (RFID) associated with the user's pill bottle in an effort to retrieve pill prescription data. Further, the processor may be operable to trigger a Near-Field Communication (NFC) unit of a pill dispenser in an effort to retrieve pill dispenser data, such that the user's ingestion of the prescription can be tracked.

In some embodiments, the processor may be operable to initialize a safety protocol and to initialize a network security protocol. In particular, multiple safety levels can be set that aligns with the medical diagnosis of the user. For example, if the user has heart disease, a safety protocol associated with the particular disease can be set by the user or the physician. Further, multiple security levels of tiered remote monitoring with date-dissemination can be provided to healthcare partners that maximize allocation and safety protocols.

Advantageously, the system and method described herein can provide a real-time remote health screening, medical monitoring, near field sharing, and fall-alert system that not only measures physical thresholds, but also recognizes harmful side-effects from prescribed drugs and send various media responses based upon vital sign descriptors. Automated and live response monitoring notifications based on biomarker anomalies such as falls, increased heart-rate, and/or instability can be provided to healthcare staff. Effectively, this system connects patients, families, and healthcare providers with an accurate, wireless biometric monitoring, screening, and measurement communications solution. Particularly, the system provides the healthcare community with pre-diagnostic screening tools, precise measuring tools and services that will ultimately yield the highest level of quality care with a reduction in expenses through the use a remote medical platform. In this way, a new standard in health monitoring that precisely substantiates physical activity and remote follow-up aftercare is provided.

In the following description, numerous details are set forth. It will be apparent, however, to one skilled in the art, that the present invention may be practiced without these specific details. In some instances, well-known structures and devices are shown in block diagram form, rather than in detail, in order to avoid obscuring the present invention.

Some portions of the detailed descriptions which follow are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, as apparent from the following discussion, it is appreciated that throughout the description, discussions utilizing terms such as "detecting," "generating," "parsing," "monitoring," "comparing," "retrieving," "triggering," "identifying", or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The present invention also relates to an apparatus for performing the operations herein. This apparatus may be specially constructed for the required purposes, or it may comprise a general purpose computer selectively activated or reconfigured by a computer program stored in the computer. Such a computer program may be stored in a computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, each coupled to a computer system bus.

Reference in the description to "one embodiment" or "an embodiment" means that a particular feature, structure, or characteristic described in connection with the embodiment is included in at least one embodiment of the invention. The phrase "in one embodiment" located in various places in this description does not necessarily refer to the same embodiment. Like reference numbers signify like elements throughout the description of the figures.

Figure 2A:
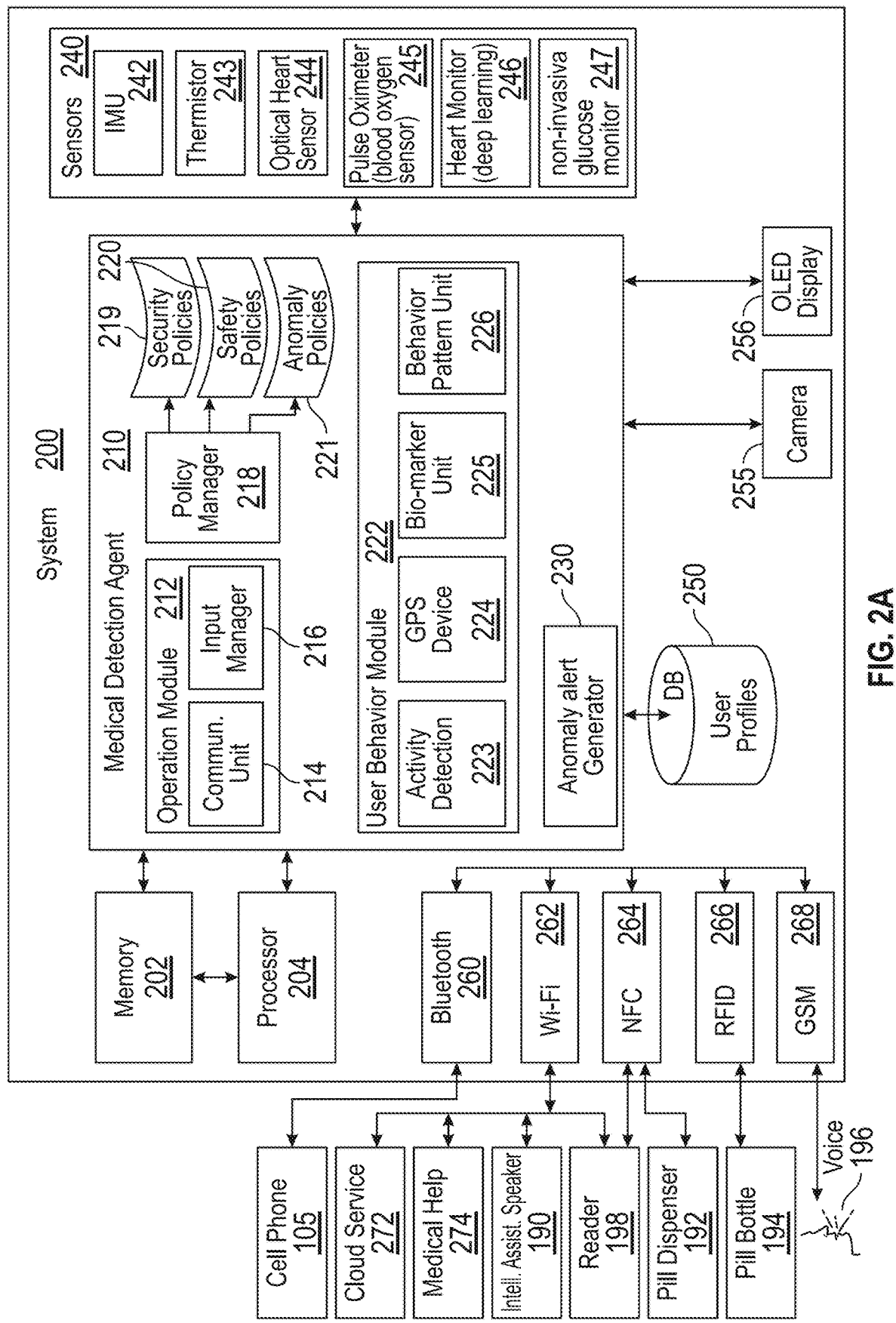
FIG. 2A is a block diagram of an exemplary system 200 included within the client node band (110, 120) of dynamic biometric detection and response within a biometric detection band of the exemplary network of FIG. 1, in accordance with some embodiments.

Referring to FIG. 1, the system diagram of an exemplary network incorporating the systems and methods of dynamic biometric detection and response, in accordance with some embodiments, is shown. The system includes at least one client node band 110, 120, a network 150, at least one monitoring server 140, and a database (not shown in FIG. 1 but shown FIG. 2A). As shown in FIG. 1, the exemplary network architecture 100 may include client nodes such as computing devices 105, and bands (110, and 120), in communication with one another and the server 140 through network 150. Each client node (band) (110, 120) may possess a medical detection agent 210, while each client node (computing device) 105 may possess a medical detection module (to be described in detail further with reference to FIGS. 2A and 2B). One or more IoT devices, such as an artificial intelligence speaker may couple to any one of the client nodes (105, 110, 120) for user-customized automation of the medical monitoring for the purpose of a voice-enabled intelligent interface to the system. Monitoring of medication intake may occur with the use of a pill dispenser coupled to the any one of the client nodes (105, 110, 120). In particular, the network 100 may include a pill dispenser 192 having a Near-Field Communications (NFC) unit that couples to any one of the client nodes (105, 110, 120). Further, the network 100 may include pill bottles that have NFC units, which couple to any one of the client nodes (105, 110, 120) to provide medical prescription data to each. Additionally, the monitoring system of each client node (105, 110, 120) may include a Global System for Mobile communications (GSM) unit (as shown in FIG. 2A) to enable voice activation. Moreover, the network may include one or more readers 198 enabled to couple to any one of the client nodes (105, 110, 120) by way of Wi-Fi communications to access and retrieve data. For example at the scene of a user emergency, a first responder can scan any one of the client nodes (105, 110, 120) worn by the user or within the user's possession using a reader 198 to access and retrieve data (such as transmitted vitals, daily prescription usage, and video) as would be appreciated by one of ordinary skill in the art having the benefit of this disclosure.

Computing devices nodes 110, 120, with local data store 240, may couple to the monitoring server 140, having its own medical detection module 310, through network 150 for the purpose of sharing and processing of data. Server 140 may couple to the storage devices 145(1-N) for reference to prior user profiles, medical history data, medical prescription data, historical anomaly data, and versions of other parameters described below. The monitoring server 140 may perform further data processing to generate qualitative and quantitative reports based upon user activity, mobility, and/or alerts provided over a predetermined time period. Although not shown, governing authorities, such as state and federal government agencies or private hospitalization institutions and networks may couple a server 140 through network 150 to provide and/or retrieve medically related data. The data provided by these authorities may be used by monitoring server 140 (medical detection module 310) and client nodes 105, 110, 120 (medical detection module 310 and medical detection agent 210) to detect an anomaly based upon the user's profile, the detected user activity, the sensed biomarkers and the identified user behavior pattern, in real time as described below. Each client node 110, 120 may include a medical detection agent 210, memory (not shown), a processor (not shown, and local data store (not shown) (to be described in detail with reference to FIG. 2A).

In some embodiments, the medical detection agent 210, having anomaly detection and alert policies, may serve as a device that communicates with the monitoring server 140 to perform the method of detecting anomalies associated with the user's behavior in real-time described more in detail below. In other embodiments, the medical detection module 310 having an anomaly detection process may communicate with each client node 110, 120 and serve as the sole agent that performs the method of anomaly detection described herein. The client nodes 105, 110, 120, server 140, and the storage device 240 may reside on the same LAN, or on different LANs that may be coupled together through the Internet, but separated by firewalls, routers, and/or other network devices. In one embodiment, client nodes 105, 110, 120 may couple to network 150 through a mobile communication network. Client nodes 105, 110, 120 may couple to network 150 through Plain Old Telephone System (POTS). In another embodiment, the client nodes 105, 110, 120, server 140, and the storage device 240 may reside on different networks. In some embodiments, the monitoring server 140 may reside in a cloud network. Although not shown, in various embodiments, the client nodes 105, 110, 120 may be notebook computers, desktop computers, microprocessor-based or programmable consumer electronics, network appliances, mobile telephones, smart telephones, pagers, radio frequency (RF) devices, infrared (IR) devices, Personal Digital Assistants (PDAs), set-top boxes, cameras, integrated devices combining at least two of the preceding devices, and the like. FIG. 1A illustrates that the medical detection agent 210 may also entirely or partially operate to communicate with called party devices having no processing components.

In some embodiments (although not shown), the network 100 may also include at least one dumb terminal, such as a landline, cell phone, pager monitor, and the like. For example, monitoring server 140 may also be coupled to a conventional telephone by the Public Switched Telephone Network (PSTN), which couple can couple to network 150.

Figure 5A:
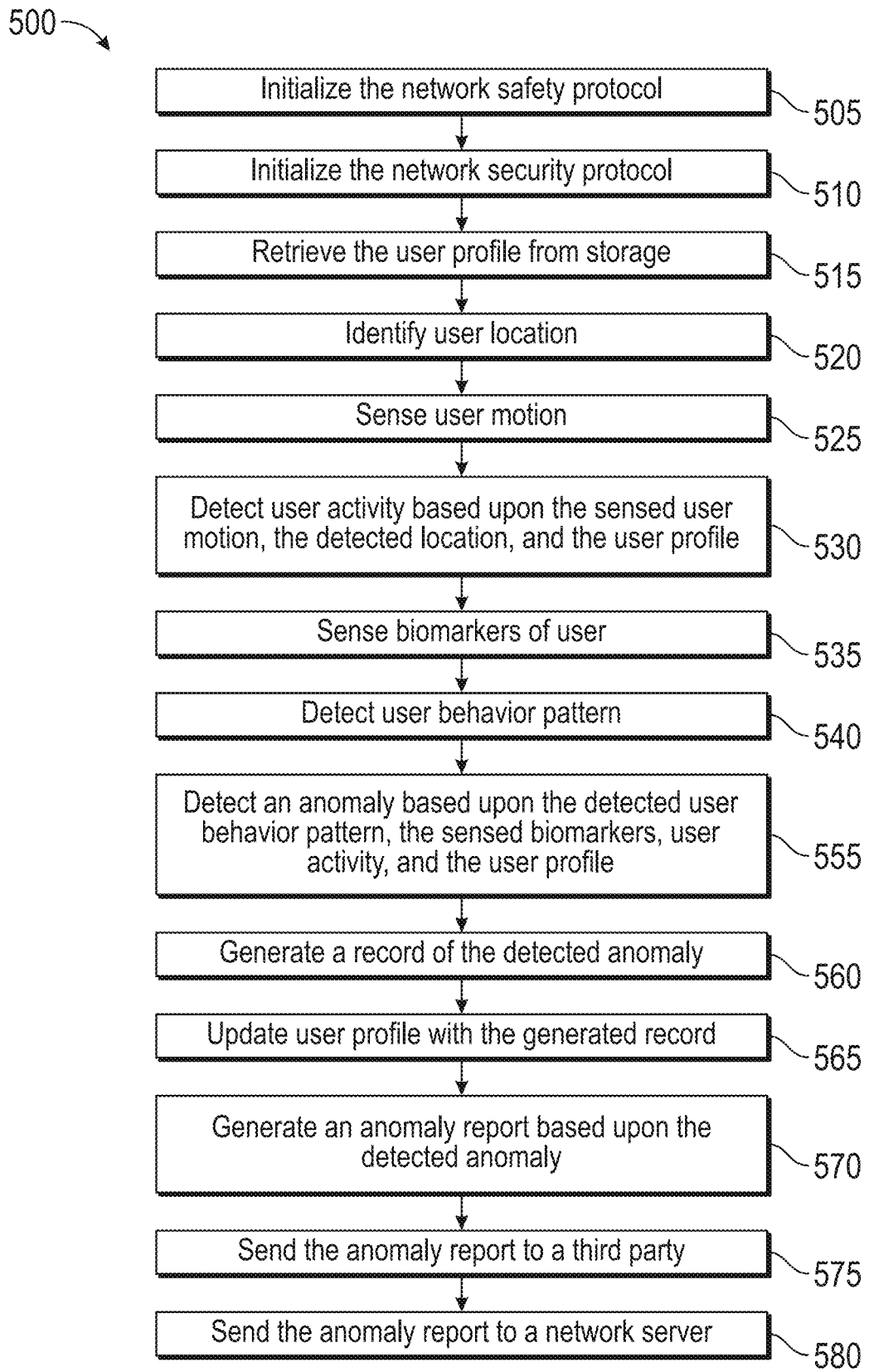
FIG. 5A is an exemplary flow diagram of a method for dynamic biometric detection and response, in accordance with some embodiments.
Figure 5B:
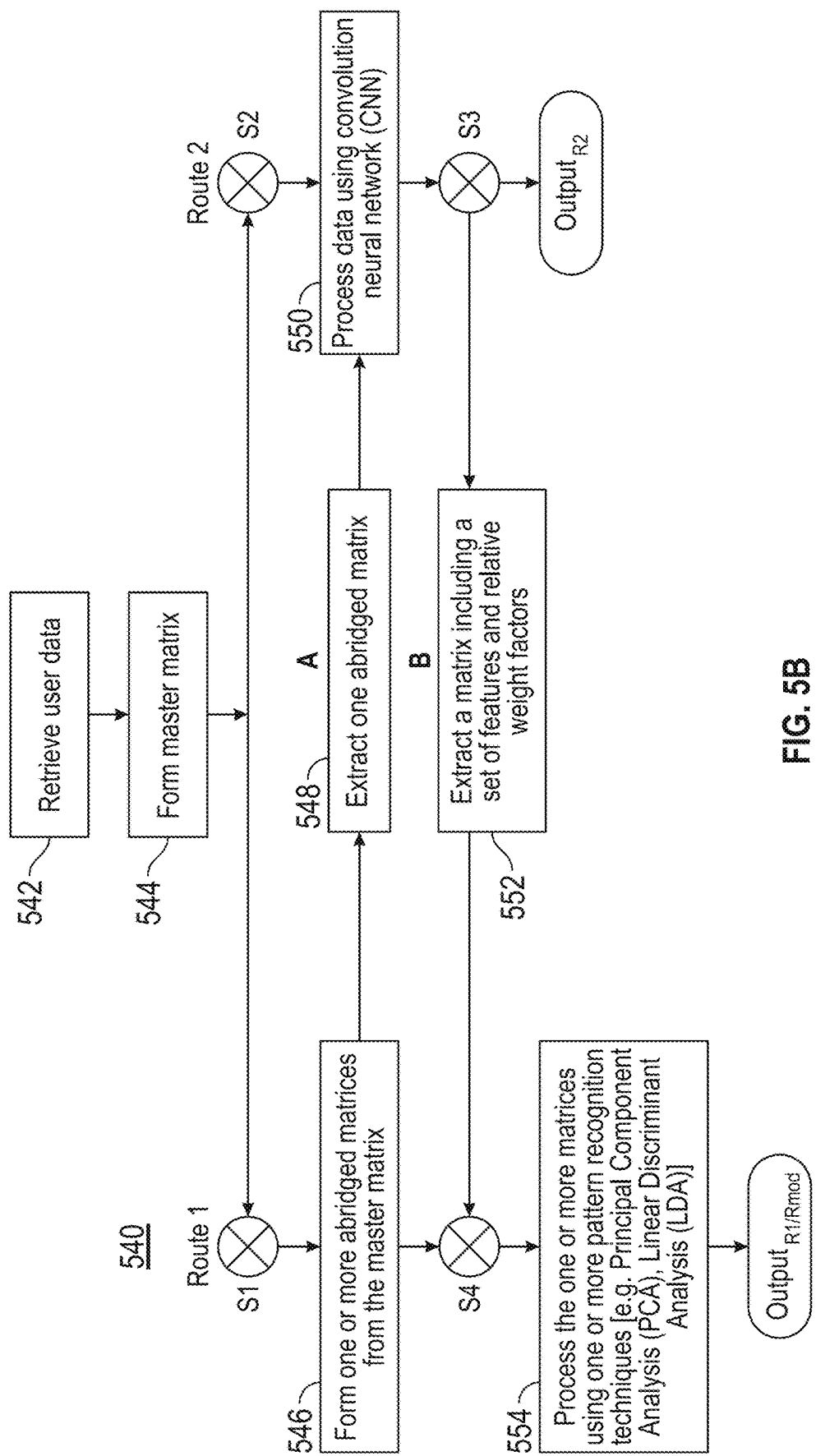
FIG. 5B is an exemplary flow diagram of a method for monitoring user activity using an enhanced machine-learning algorithm to identify repetitive actions in user behavior pattern of FIG. 5A (step 540), in accordance with some embodiments.

All or a portion of network architecture 100 may perform and/or be a means for performing, either alone or in combination with other elements, one or more of the steps disclosed herein (such as one or more of the steps illustrated in FIGS. 5A, 5B). In one example, monitoring bands 110, 120 may be programmed with one or more of modules 200 (described in detail below). In another example, computing device 105 may be programmed with one or more of modules 300 (described in detail below). Additionally or alternatively, server 140 may be programmed with one or more of modules 300. Although not shown, in various embodiments, the client node (105) including system 300 may be notebook computers, desktop computers, microprocessor-based or programmable consumer electronics, network appliances, mobile telephones, smart telephones, pagers, radio frequency (RF) devices, infrared (IR) devices, Personal Digital Assistants (PDAs), set-top boxes, cameras, integrated devices combining at least two of the preceding devices, and the like.

Client systems 105, 110, and 120 generally represent any type or form of computing device or system, such as exemplary computing system 500 in FIG. 5. Similarly, server 140 generally represents computing devices or systems, such as application servers or database servers, configured to provide various database services and/or run certain software applications. Network 150 generally represents any telecommunication or computer network including, for example, an intranet, a WAN, a LAN, a PAN, or the Internet. In one example, client systems 105, 110, and/or 120 and/or server 140 may include all or a portion of system 200 from FIG. 2A. In particular, client system 105 and/or server 140 may include all or a portion of system 300 from FIG. 2B.

The monitoring server 140 may comprise a processor (not shown), memory (not shown), and medical detection module 310. In some embodiments, the monitoring server 140 may comprise processing software instructions and/or hardware logic required for dynamic biometric detection and response according to the embodiments described herein. The monitoring server 140 may provide remote cloud storage capabilities for call classifications, call filters, and various types of anomaly policies associated, through the storage device 160 coupled by network 150. In addition the monitoring server 140 may provide remote storage capabilities for user profile data. Further, monitoring server 140 may couple to one or more tape-out devices (not shown) or any other secondary datastore. As such, a database of user profile data and anomaly policies may be stored within a local data store, remote disks, secondary data storage devices, or tape-outs devices (not shown). In some embodiments, the client nodes 105, 110, 120 may retrieve previous results relating to user profile data and anomaly policies relating to user behavior patterns from a remote datastore to a local data store (not shown). In other embodiments, the database of anomaly policies, prior detection results, medical history data, and the like may be stored locally on the client nodes 105, 110, 120 or the monitoring server 140. In particular, for remote storage purposes, the local data storage unit (not shown) can be one or more centralized data repositories having mappings of respective associations between each fragment data and its location within remote storage devices. The local data store may represent a single or multiple data structures (databases, repositories, files, etc.) residing on one or more mass storage devices, such as magnetic or optical storage based disks, tapes or hard drives. This local data store may be an internal component of the monitoring server 140. In the alternative, the local data store 145 (1-N) also may couple externally to monitoring server 140 as shown in FIG. 1, or remotely through a network 160 (storage devices 170(1-N)). Further, the monitoring server 140 may communicate with the remote storage devices over a public or private network. Although not shown, in various embodiments, the monitoring server 140 may be a notebook computer, desktop computer, microprocessor-based or programmable consumer electronics, network appliance, mobile telephone, smart telephone, radio frequency (RF) device, infrared (IR) device, Personal Digital Assistant (PDA), set-top box, an integrated device combining at least two of the preceding devices, and the like.

In some embodiments, one or more storage devices 145 (1)-(N) may be directly attached to server 140. Storage devices 145(1)-(N) generally represent any type or form of storage device or medium capable of storing data and/or other computer-readable instructions. In certain embodiments, storage devices 145(1)-(N) may represent Network-Attached Storage (NAS) devices configured to communicate with server 140 using various protocols, such as Network File System (NFS), Server Message Block (SMB), or Common Internet File System (CIFS).

Server 140 may also be connected to a Storage Area Network (SAN) fabric 160. SAN fabric 160 generally represents any type or form of computer network or architecture capable of facilitating communication between a plurality of storage devices. SAN fabric 160 may facilitate communication between server 140 and a plurality of storage devices 170(1)-(N) and/or an intelligent storage array 180. SAN fabric 160 may also facilitate, via network 150 and server 140, communication between client systems 105, 110, and 120, and storage devices 170(1)-(N) and/or intelligent storage array 180 in such a manner that devices 170(1)-(N) and array 180 appear as locally attached devices to client systems 110 and 120.

Figure 6:
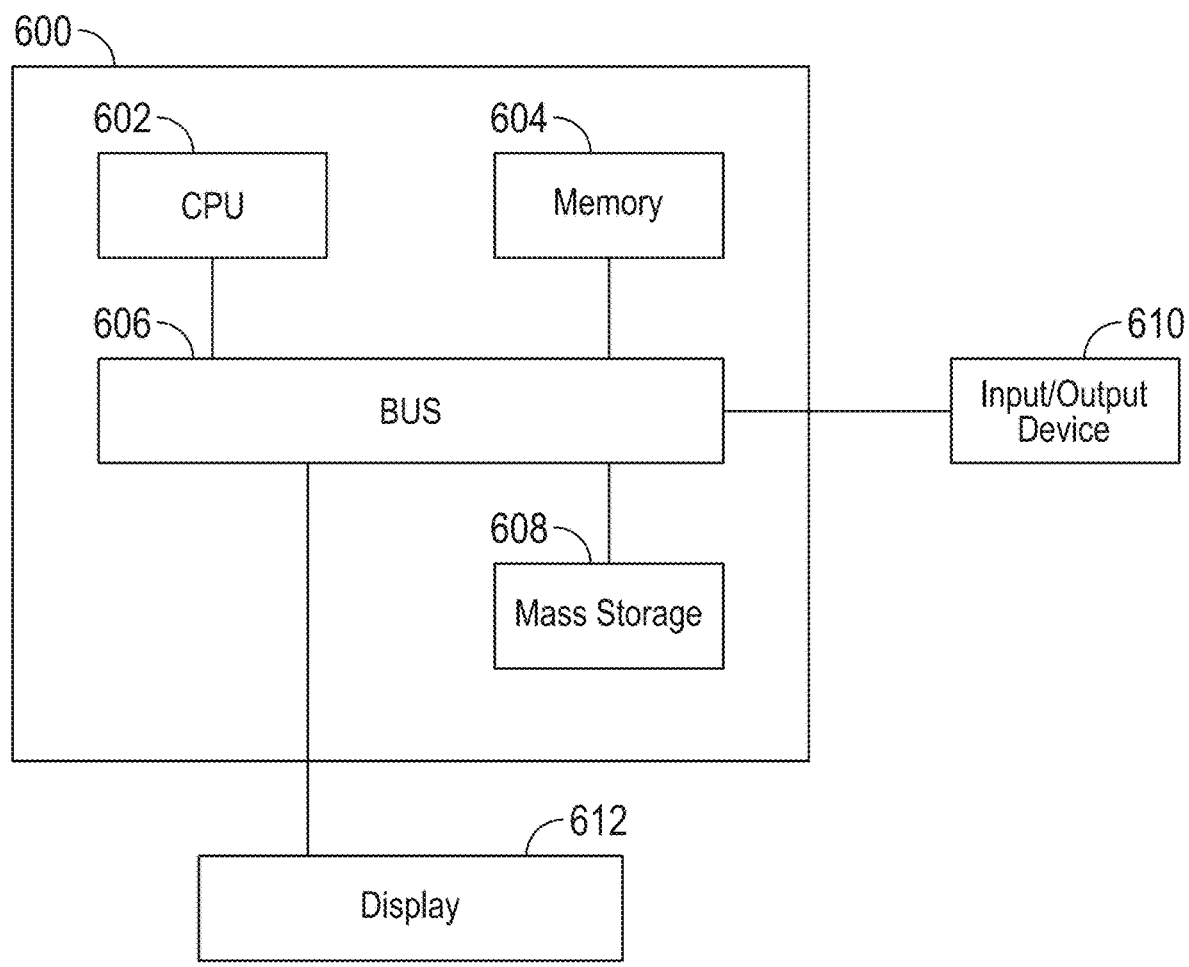
FIG. 6 is an illustration showing an exemplary computing device, which may implement the embodiments described herein.

In certain embodiments, and with reference to exemplary computing system 500 of FIG. 6, a communication interface may be used to provide connectivity between each client system 105, 110, and 120 and network 150. Client systems 105, 110, and 120 may be able to access information on server 140 using, for example, a web browser or other client software. Such software may allow client systems 105, 110, and 120 to access data hosted by server 140, storage devices 145(1)-(N), storage devices 170(1)-(N), or intelligent storage array 180. Although FIG. 1 depicts the use of a network (such as the Internet) for exchanging data, the embodiments described and/or illustrated herein are not limited to the Internet or any particular network-based environment.

In at least one embodiment, all or a portion of one or more of the exemplary embodiments disclosed herein may be encoded as a computer program and loaded onto and executed by server 140, storage devices 145(1)-(N), storage devices 170(1)-(N), or intelligent storage array 180, or any combination thereof. All or a portion of one or more of the exemplary embodiments disclosed herein may also be encoded as a computer program, stored in server 140, and distributed to client systems 105, 110, and 120 over network 150.

In operation, the medical detection agent 210 may communicate with the network 150 to initiate a safety protocol that ensures the safety of the user based upon the user's medical condition. Further, the medical detection agent 210 may initiate a security protocol for the purpose of protecting the privacy of each user's medical records prior to retrieval of user profile data. For example, the medical detection agent 210 may retrieve a user profile from a local storage unit or a remote storage unit (145(1-N), 170(1-N)). Next, the medical detection agent 210 may identify user's location by accessing a GPS unit (not shown) located within the medical detection agent 210. For example, the medical detection agent 210 may be able to sense one or more satellite signals within a GPS network. From this sensed signal, the medical detection agent 210 may be able to detect the travel time of the sensed signal and calculate the distance between the medical detection agent 210 and at least one satellite using the travel time. From this distance, the medical detection agent 210 can calculate the user's location.

Further, the medical detection agent 210 may be able to sense the user's motion. Sensing user motion may occur by retrieval of at least one of the user's specific force, angular rate, or orientation using an IMU (not shown) located within the medical detection agent 210. The medical detection agent 210 may utilize 360-imaging of a camera for calculation of fall detection and for providing real-time visual perspective of the user's surroundings. Particularly, a band having the medical detection agent 210 worn band/device will simultaneously record and calculate fall detection using inertia movements and visual data using optical sensor data inputs, in an effort to report real-time prescription drug usage and body-emitting vitals to be shared and immediately transmitted to secure readers and/or IoT device and machine learning/cloud platforms connected through an array of secure, access granted, software and hard-ware linked platforms (such as RFID, NFC, BLE, WI-FI and/or, cellular infrastructure to be described in more detail with respect to FIG. 2A).

In some embodiments, based upon the user profile, the sensed user location, and sensed user motion, the medical detection agent 210 may detect the user's activity. For example, the medical detection agent 210 may parse the user profile to identify a predetermined set of locations, and associated activities, wherein each activity includes a corresponding motion. From a comparison of the detected location with the predetermined set of locations, the medical detection agent 210 can compare the sensed user motion with the corresponding motion of the matched location and set the matched motion to be the detected user activity. In the alternative, user activity may be detected based upon the user motion.

Further, the medical detection agent 210 may sense the biomarkers of user. For example, in some embodiments the medical detection agent 210 may retrieve one or more to the following: the user's temperature from a thermistor; the user's blood pressure from a sensing unit having a deep learning algorithm associated with monitoring heart rate; the user's blood oxygen level from a pulse oximeter blood oxygen sensor; the user's blood glucose level from a non-invasive glucose monitor; and the user's pulse from an optical heart sensor. Additionally, the medical detection agent 210 may detect user behavior pattern. For example, the medical detection agent 210 may monitor the user activity and motion using advanced machine-learning algorithms, including principal component analysis and neural network computations. Moreover, based upon the detected user behavior pattern, the sensed biomarkers, user activity, and the user profile, the medical detection agent 210 may be operable to detect an anomaly in user behavior. Finally, the medical detection agent 210 may generate an anomaly alert for third party notification and/or quantitative analysis at a server.

In some embodiments, the medical detection agent 210 may be able to communicate with a pill dispenser using a NFC unit in order to retrieve up-to-date information on levels of medication available. Similarly, the medical detection agent 210 can also communicate with RFID tags to retrieve pill bottle prescription data in an effort to update the user profile.

When the user has experienced trauma or a fall, first responders with a reader may be able to access and retrieve the dynamic biometric data retrieved. Physicians, with a reader may be able to access and retrieve medical data when the user visits the doctor for an appointment.

In some embodiments, the medical detection agent 210 may be use to collect and transmit a balanced combination of data associated with the user. For example, medical detection agent 210 may collect data relating to the user's location (e.g. home, malls, driving on the road or walking in parks and the like); user motion (e.g. sitting, standing, walking, running, rotation and jumping, and the like, including speed, acceleration and strength of motion); user's daily living routine (sleeping, dining, medication schedule, and the like); user's bio-markers (e.g. the heartbeat, blood oxygen level, blood pressure, temperature, and the like); and time periods associated with these. The medical detection agent 210 can use this data to build an active profile model of daily activities for the users. Such a model includes intertwined array of the users' measure of central tendency bio-marker indications, reactions to prescription drugs, and daily physical habits in exercise and body mechanics, sleeping and dining routines, body conditions, daily living schedules, and the like. The parameters of the model can be stored in a matrix of a local database of the medical detection agent 210, wherein multiple dimensions can be stored. For example, the following matrix having 72×2850 elements may describe the model for a user.

$$R = \begin{bmatrix} R_{1,1} & R_{1,2} & \ldots & R_{1,2849} & R_{1,2850} \\ R_{2,1} & R_{2,2} & \ldots & R_{2,75} & R_{2,2850} \\ \vdots & \vdots & \ddots & \vdots & \vdots \\ R_{71,1} & R_{71,2} & \ldots & R_{71,2849} & R_{71,2850} \\ R_{72,1} & R_{72,2} & \ldots & R_{72,2849} & R_{72,2850} \end{bmatrix}$$

In some embodiments, the matrix can be used to precisely determine whether an anomaly exists and generate an anomaly alert signal and/or report. In addition, the model can be an evolving model, wherein the medical detection agent 210 continuously learns the user's routine schedule and bio-dynamics; and thereby, adjusts the parameters of the matrix comparisons of the existing parameter matrix and the newly collecting data. In some embodiments, medical detection agent 210 may use principle component analysis (PCA) to determine the change and difference between the existing model and new routine/behavior (to be described in more detail with reference to FIG. 3). In some embodiments, the medical detection agent 210 may use neural network analysis to detect an anomaly in the user's behavior. If such a difference is repeatable, the medical detection agent 210 will add the new set of data to the existing model.

In some embodiments for example, an elderly user, who usually takes a walk after dinner may have an average heartbeat of 80 beats per minute as a normal condition. However, an alarm can be generated if the user has a heartbeat below 65 while walking outside, even though the senior user usually has heartbeat below 65 while resting at home. In addition, prescription usage bio-marker side-effects and/or reactions may be included and cross-referenced within the alert.

In another example, a user usually may have a blood oxygen level from 75 to 100 mm Hg from resting to exercising. In operation, the medical detection agent 210 can cross-reference composite data points and generate an alarm if the user has a blood oxygen level below 80 while the user has an active body motion in an unexpected schedule determined by the model. The medical detection agent 210 can discover an abnormal condition.

It is appreciated that the components of exemplary operating environment 100 are exemplary and more or fewer components may be present in various configurations. It is appreciated that operating environment may be part of a distributed computing environment, a cloud computing environment, a client server environment, and the like.

In other words, as would be apparent to one of ordinary skill in the art after reading this description, the various features and functionality described herein may be implemented in the computing device architecture using any arrangement components necessary to perform the dynamic biometric detection and response features (and functionality); and can be implemented in one or more separate or shared modules in various combinations and permutations.

As used herein, the terms agent and module might describe a given unit of functionality that can be performed in accordance with one or more embodiments of the present invention. As used herein, an agent or module might be implemented utilizing any form of hardware, software, or a combination thereof. For example, one or more processors, controllers, ASICs, PLAs, PALs, CPLDs, FPGAs, logical components, software routines or other mechanisms might be implemented to make up the agent or module. In implementation, the various agents and modules described herein might be implemented as discrete modules or the functions and features described can be shared in part or in total among one or more modules. In other words, as would be apparent to one of ordinary skill in the art after reading this description, the various features and functionality described herein may be implemented in any given application and can be implemented in one or more separate or shared agents or modules in various combinations and permutations. Even though various features or elements of functionality may be individually described or claimed as separate agents and modules, one of ordinary skill in the art will understand that these features and functionality can be shared among one or more common software and hardware elements, and such description shall not require or imply that separate hardware or software components are used to implement such features or functionality.

Referring now to FIG. 2A, a block diagram of an exemplary system for dynamic biometric detection and response within a biometric detection band of the exemplary network of FIG. 1, in accordance with some embodiments is presented. Exemplary system 200 may be implemented in a variety of ways. For example, all or a portion of exemplary system 200 may represent portions of exemplary network 100 in FIG. 1. As illustrated in FIG. 1, exemplary system 200 may include a memory 202, a processor 204, and a storage database 250. The system may include one or more medical detection agents 210 for performing one or more tasks. For example, and as will be explained in greater detail below, medical detection agent 210 may include an operations module 212; a policy manager 218 with associated security policies 219, safety policies 220, and anomaly policies 221; a user behavior module 222; and an anomaly alert generator 230. The operations module 212 can include a communications unit 214 for generating communication signals to receive and transport medical data. The operations module 212 can further include an input manager 216 for the display unit 256 that detects whether the user has fallen based upon a snap shot view of the camera 255, when a fall is detected. The policy manager 218 in collaboration with a user profile may select safety standards from the safety policies 220 that align with the user's medical prognosis (i.e. a safety policy for a senior, a diabetic, a heart disease patient, an Alzheimer's patient, a person with Attention Deficit Disorder (ADD), and the like). Further, the policy manager 218 may select security rules from the security policies 219 for the purpose of protecting the privacy of each user's medical records based upon the user's profile and the latest revision of the Health Insurance Portability and Accountability Act (HIPPA) laws, which mandate that organizations working with Protected Health Information (PHI) implement technical, physical, and administrative safeguards to protect sensitive information.

In some embodiments, the user behavior module 222 may include an activity detection unit 223, a GPS device 224, a bio-marker unit 225, and a behavior pattern unit 226. The activity detection unit 223 can be used to detect the activity of the user based upon the sensed user motion, the detected location, and the user profile. For example, in some embodiments the activity detection unit 222 in collaboration with the processor 204 may be able to retrieve and to parse the user profile to identify a predetermined set of locations, and associated activities, wherein each activity having a corresponding motion. From a comparison of the detected location with the predetermined set of locations, the activity detection unit 223 can compare the sensed user motion with the corresponding motion of the matched location to identify the activity of the user. Further, the GPS device 224 can be used to detect the location of the user. For example, in some embodiments the processor 204 in cooperation with GPS device 224 may be able to sense one or more satellite signals within the GPS; detect the travel time of the signal; calculate the distance between the processor and at least one satellite; and calculate the user location based upon this distance. Additionally, the bio-marker unit 225 can be used to translate the data from the sensors 240 for entry into the anomaly alert generator 230 and the database 250 (for the purpose of updating the user profile). Initially, the behavior pattern unit 226 can be used to detect a pattern in the behavior of the user. For example, the behavior pattern unit 226 may monitor the user activity using advanced machine-learning algorithms, including principal component analysis and neural network computations. The behavior pattern unit 226 may identify repetitive actions in an effort to detected one or more user behavior patterns.

In cooperation with the medical detection agent 210, the system 200 may include a sensor unit 240 having one or more of the following sensors: IMU 242, thermistor 243, optical heart sensor 244, pulse oximeter (blood oxygen sensor) 245, heart monitor (deep learning) 246, and non-invasive glucose monitor 247. The system 200 can also include one or more of the various communication utilities: Bluetooth 260, Wi-Fi 262, NFC 264, RFID 266, and GSM 268. Further, the system 200 can exchange information with other client nodes 105.

In operation, the processor 204 in collaboration with the policy manager 218 may communicate with the network 150 to initiate a safety protocol of the safety policies 220 that ensures the safety of the user based upon the user's medical condition. Further, the processor 204 in collaboration with the policy manager 218 may initiate a security protocol 219 for the purpose of protecting the privacy of each user's medical records prior to retrieval of user profile data. For example, multiple security levels of tiered remote monitoring with data-dissemination can be provided to healthcare servers, maximizing allocation and safety protocols. In particular, the processor 204 in collaboration with the operation module 212 may retrieve a user profile from a local storage unit 250. Next, the processor 204 in collaboration with the user behavior module 212 may identify the user's location by actuating the GPS unit 224. For example, the processor 204 in collaboration with the bio-marker unit 225 may be able to sense one or more satellite signals within a GPS network. From this sensed signal, the GPS unit 224 may be able to detect the travel time of the sensed signal and calculate the distance between the GPS unit 224 and at least one satellite using the travel time. From this distance, the GPS unit 224 can calculate the user's location.

Further, the medical detection agent 210 in collaboration with the IMU 242 may be able to sense the user's motion. For example, sensing user motion may occur by retrieval of at least one of the user's specific force, angular rate, or orientation from the IMU 242 located within the medical detection agent 210. Based upon the user profile, the sensed user location, and sensed user motion, the activity detection unit 223 may detect the user's activity. For example, the activity detection unit 223 may parse the user profile to identify a predetermined set of locations, and associated activities, wherein each activity includes a corresponding motion. From a comparison of the detected location with the predetermined set of locations, the activity detection unit 223 can compare the sensed user motion with the corresponding motion of the matched location and set the matched motion to be the detected user activity. In the alternative, user activity may be detected based upon the sensed user motion directly form the IMU 242.

Further, the bio-marker unit 225 may detect the biomarkers of the user using the various sensors (243, 244, 245, 246, and 247) of the sensing unit 240. For example, in some embodiments the processor 204 in collaboration with the bio-marker unit 225 may retrieve one or more to the following: the user's temperature from a thermistor 243; the user's blood pressure from a sensing unit having a deep learning algorithm associated with monitoring heart rate; the user's blood oxygen level from a pulse oximeter blood oxygen sensor 245; the user's blood glucose level from a non-invasive glucose monitor 247; and/or the user's pulse from an optical heart sensor 244. In some embodiments, the bio-marker unit 225 may retrieve user input, including keyboard data input or voice input relating to psychological data, such as any data relating to their emotional or physical state. Additionally, the behavior pattern unit 226 may detect user behavior pattern. For example, the behavior pattern unit 226 may monitor the user activity and motion using advanced machine-learning algorithms, including principal component analysis and neural network computations. Moreover, based upon the detected user behavior pattern, the sensed biomarkers, user activity, and the user profile, the anomaly alert generator 230 in collaboration with the policy manager 218 may be operable to detect an anomaly in user behavior based upon the anomaly policies 221. Finally, the anomaly alert generator 230 may generate an anomaly alert for third party notification and/or quantitative analysis at a server 140.

In some embodiments, the medical detection agent 210 may be able to communicate with a pill dispenser 196 using a NFC unit 264 in order to retrieve up-to-date information on levels of medication available. Similarly, the medical detection agent 210 can also communicate with RFID tags using the RFID unit 266 to retrieve pill bottle 194 prescription data in an effort to update the user profile. Additionally, the system 200 may communicate with a cloud service 272 for a cloud-based software service; a medical help utility 274 for first responder data exchange; and an intelligent assist speaker (IoT devices) 276 for user-customized automation of the medical monitoring for the purpose of a voice-enabled intelligent interface 196 to the system. The communication utilities may include modulated frequency streams such as, LTE, 5G, WiFi, Bluetooth, NFC, and/or SMT. In some embodiments, the user may use the keyboard or his voice to enter in psychological data, such as any data relating to their emotional or physical state.

In some embodiments, the sensed bio-markers may be displayed on the display 256. Further, the outputs generated by the user behavior module 222 and anomaly alert generator 230 may be displayed on display 256. Additionally, system 200 may include a mechanical or electrical power generator to provide power necessary for the system.

Figure 2B:
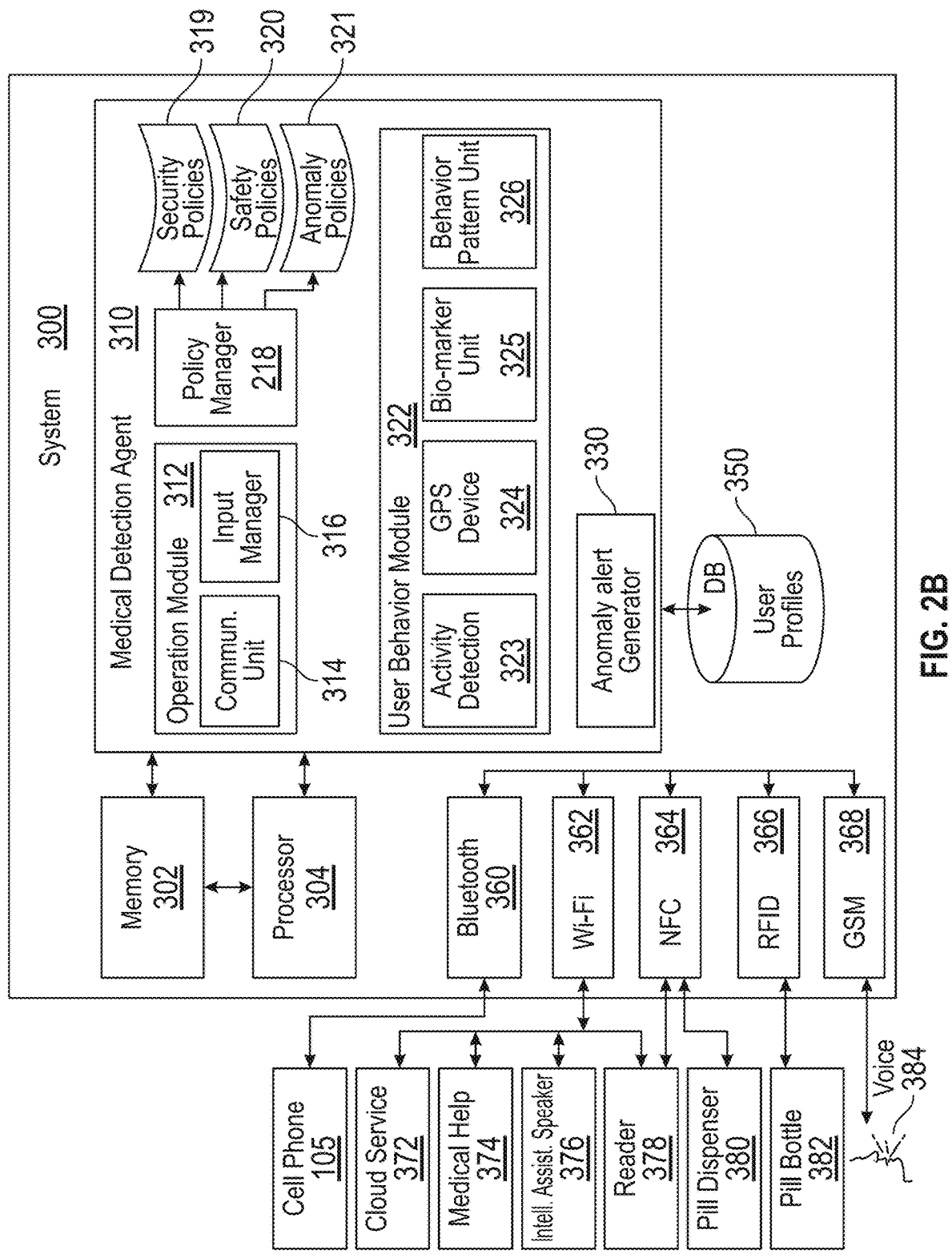
FIG. 2B is a block diagram of a system 300 included within the client node device or server (105, 140) of dynamic biometric detection and response within a mobile device and server of the exemplary network of FIG. 1, in accordance with some embodiments.

Referring now to FIG. 2B, a block diagram of another system 300 for dynamic biometric detection and response within a mobile device and server of the exemplary network of FIG. 1, in accordance with some embodiments is illustrated. Similar to the system 200, system 300 may include memory 302, processor 304, medical detection module 310, local database 350, Bluetooth 360, Wi-Fi 362, NFC 364, RFID 366, and GSM 368. The medical detection module 310 differs from the medical detection agent 210 of FIG. 2A in that it does not include a sensor unit such as unit 240 disclosed in FIG. 2A. Further, similar to system 200, system 300 may include an interface for communication with a cloud service 372; a medical help utility 374; an intelligent assist speaker (IoT devices) 376; a reader 378; a pill dispenser 380, pill bottle 382; and voice-enabled instruction 384.

In operation, system 200 may exchange data with system 300 in an effort to detect user location, user activity, user behavior patterns, and anomalies. As noted supra, the various agents 210 and modules 310 described herein can be implemented as discrete modules or the functions and features described can be shared in part or in total among one or more modules or agents. In other words, as would be apparent to one of ordinary skill in the art after reading this description, the various features and functionality described herein may be implemented in any given application and can be implemented in one or more separate or shared agents or modules in various combinations and permutations. Even though various features or elements of functionality may be individually described or claimed as separate agents and modules, one of ordinary skill in the art will understand that these features and functionality can be shared among one or more common software and hardware elements, and such description shall not require or imply that separate hardware or software components are used to implement such features or functionality.

Figure 3:
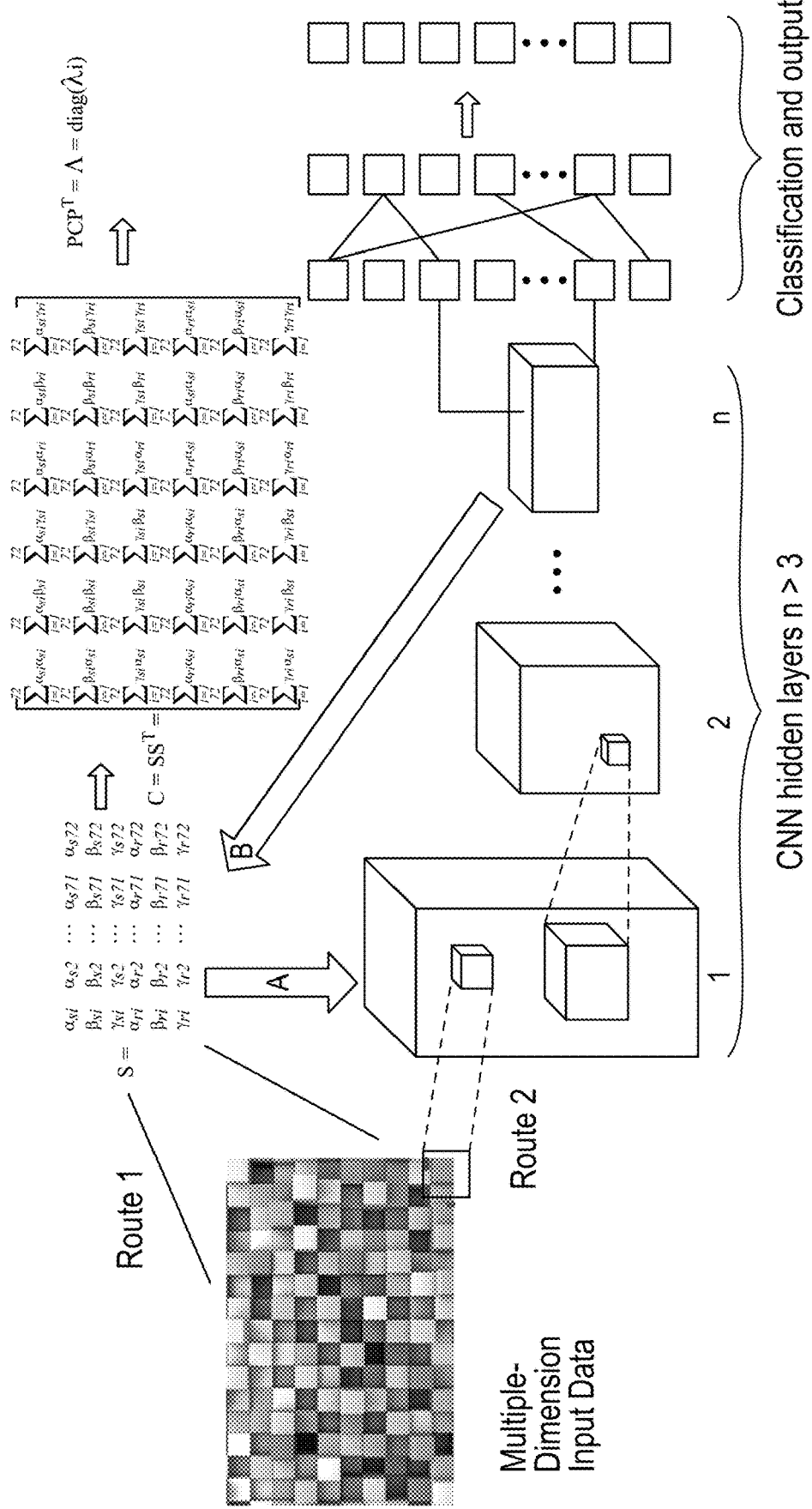
FIG. 3 is a block diagram of an enhanced machine-learning algorithm for identifying repetitive actions within the user's behavior pattern used by the Behavior Pattern Unit FIG. 2A (226) of the medical detection agent 210 of FIG. 1, in accordance with some embodiments.

Referring now to FIG. 3, a block diagram of an enhanced machine-learning algorithm for identifying repetitive actions within the user's behavior pattern, in accordance with some embodiments is shown. In particular, this novel technique can be implemented within the Behavior Pattern Unit FIG. 2A (226) of the medical detection agent 210 of FIG. 1. As noted supra, the system and method of dynamic biometric detection and response may detect and record a comprehensive set of user data. In particular, real-time location data (home, driving, office, malls or recreation places); motion (sitting, standing, walking, running, rotation and jumping, whereby speed, acceleration and strength of the motion can be calculated); daily living state information (sleeping, drinking, dining, enjoying music, watching movies, and medication schedule), body status (heartbeat, blood oxygen level, blood pressure), and time (time and time periods of aforementioned activities) can be detected or received from the user as input. Further, the user may use the voice interface 196 or the keyboard of the mobile device 105 to enter the emotional state, by either selecting a numerical value or entering words associated with their emotions (e.g. a number from "0" (least) to "10" (best); or "euphoric").

As shown in FIG. 3, the data can be constructed as multiple-dimension matrices of data. In some embodiments, one of the two routes (Route 1 or Route 2) can be used to process the data and identify the normal or abnormal status of the user. Particularly, S represents the matrix of features extracted from the multiple-dimension input data. The variables, $\alpha$, $\beta$, and $\gamma$, represent a typical feature at a different time sampling sequence (s) or recovering sequence (r). Matrix c is derived from the multiplication of matrix S with its rotating matrix along the diagonal direction (ST). Matrix P is derived from the diagonalization of matrix c. Variable n represents the number of hidden layer of the CNN model.

In operation during Route 1, the data can be examined and a set of features can be extracted using one or more linear, polynomial, or exponential formulas to form matrices with less dimensions. In some embodiments, the size of data can be shrunk to 1/10 of the original data. Next, the extracted feature matrices can be processed by manipulation of the data and pattern recognition. In particular, some embodiments may employ the use of the modified principal component analysis (PCA) and Linear Discriminant Analysis (LDA) of linear algebra, to identify the user's current health and abnormally conditions. In contrast, the operation during the route 2 may include directly processing the original data using a machine learning technique, such as employing the use of a convolutional neural network (CNN). From this type of analysis the classification and identification of user's situation can be derived.

Beneficially, the Route 1 method has the advantage of computation efficiency and fast processing speed. The disadvantage, however, is that the method of Route 1 can be of relatively low precision. In contrast, the method of Route 2 can be quite precise but may require a large amount of computation resources (CPU time and memory cells) and consume a much longer computation time.

In some embodiments, the system and method for dynamic biometric detection and response uses an enhanced algorithm whereby two connections (A and B) are made between Route 1 and 2 to significantly improve the accuracy and computation efficiency. In particular with reference to route A, a set of comprehensive features can be extracted as the input data for machine learning using neural network computation analysis. Since the feature input data is much smaller in size than the original data, the machine learning computation will be much faster and consume less computation resources, while the accuracy is maintained. During route B, the original data can be processed using machine-learning, such as CNN to extract a set of more representative features and related weight factors. These extracted features will be more precise and comprehensive then the features extracted by a set of fixed formulas. Accordingly, these extracted data can then be used as input data for PCA or LDA matrix manipulation in an effort to identify and classify the users' state.

Figure 4A:
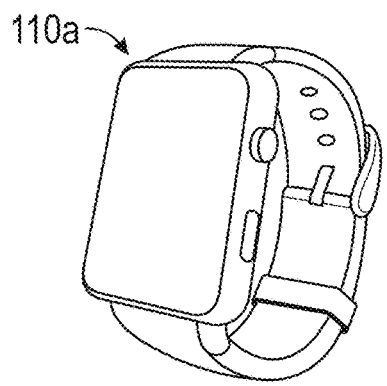
FIG. 4A is a perspective view of the front of a wristband 110a of the exemplary network of FIG. 1, in accordance with some embodiments.
Figure 4B:
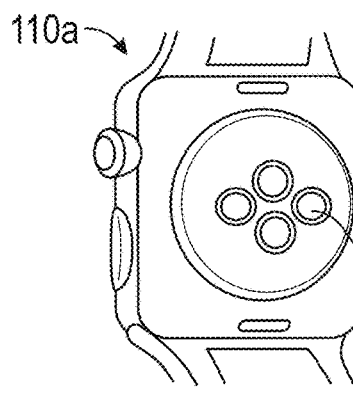
FIG. 4B is a perspective view of the back of the wristband 110a of the exemplary network of FIG. 1, in accordance with some embodiments.

Referring now to FIG. 4A, a perspective view of the front of a wristband 110*a* of the exemplary network of FIG. 1, in accordance with some embodiments is shown. The wristband (D-Band™) is a wearable monitoring device, having system 200 of FIG. 2A, that is worn on the wrist, where the user's heart rate (pulse), blood pressure, blood glucose level, temperature, and blood oxygen are precisely monitored and measured. Detection of falls and biomarkers can be all conveyed wirelessly in real-time. As shown in FIG. 4B, a perspective view of the back of the wristband 110*a* of the exemplary network of FIG. 1, illustrates that various sensors can be embedded into the wristband 110*a*. These may include various types of sensors in direct and indirect contact with the user; including, IMU 242, thermistor 243, optical heart sensor 244, pulse oximeter (blood oxygen sensor) 245, heart monitor (deep learning) 246, and non-invasive glucose monitor 247. The system 200 within the wristband 110*a* can include one or more of the various communication utilities: Bluetooth 260, Wi-Fi 262, NFC 264, RFID 266, and GSM 268. Further, the system 200 within the waistband 110*a* can exchange information with other client devices 105.

Figure 4C:
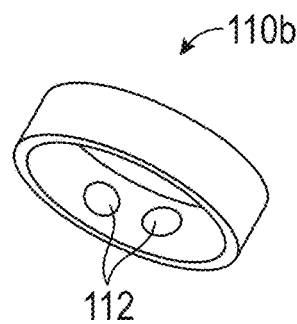
FIG. 4C is a perspective view of a ring 110b of the exemplary network of FIG. 1, in accordance with some embodiments.

Referring now to FIG. 4C, a perspective view of a ring 110*b* of the exemplary network of FIG. 1, in accordance with some embodiments, is displayed. The ring 110*b* is a wearable monitoring device, having system 200 of FIG. 2A, that is worn on the finger where the user's heart rate (pulse), blood pressure, blood glucose level, temperature, and blood oxygen are precisely monitored and measured. Similar to the wristband 110*a*, the ring 110 includes system 200 of FIG. 2A. In particular, the band 110*b* may be in the form of a ring (D-Ring™) to be worn around the user's finger, serving as a wearable monitoring device that works in concert with the wristband and within an established healthcare network. In particular, key biomarkers can be monitored and communicated within the network through the use of the ring. Similarly, ring 110b may include various types of sensors 112, representing one or more of the various sensors to the IMU 242, thermistor 243, optical heart sensor 244, pulse oximeter (blood oxygen sensor) 245, heart monitor (deep learning) 246, and non-invasive glucose monitor 247 shown in FIG. 2A. The system 200 within the ring 110b can include one or more of the various communication utilities: Bluetooth 260, Wi-Fi 262, NFC 264, RFID 266, and GSM 268. Further, the system 200 within the ring 110b can exchange information with other client devices 105.

Figure 4D:
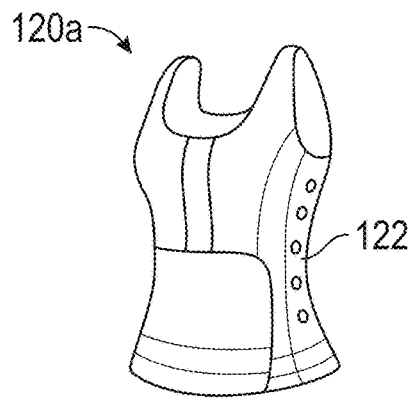
FIG. 4D is a perspective view of the front of a vest 120a of the exemplary network of FIG. 1, in accordance with some embodiments.
Figure 4E:
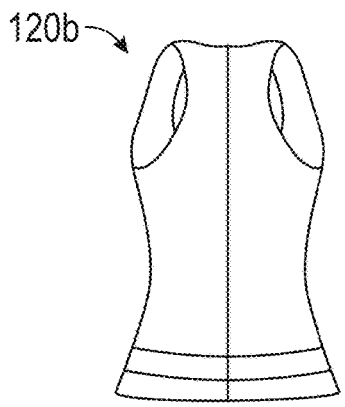
FIG. 4E is a perspective view of the back of the vest 120a of the exemplary network of FIG. 1, in accordance with some embodiments.
Figure 4F:
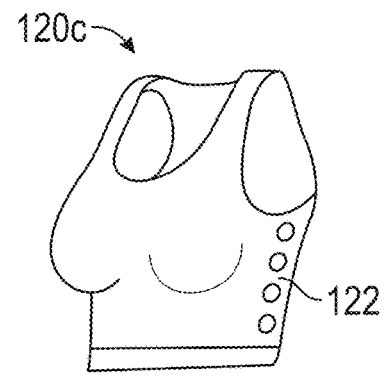
FIG. 4F is a perspective view of the vest 120c of the exemplary network of FIG. 1, in accordance with some embodiments.

Referring now to FIGS. 4D and 4E, a perspective view of the respective front and back of a vest 120a of the exemplary network of FIG. 1, in accordance with some embodiments is illustrated. The vest 120a may include a wearable monitoring device (including system 200 of FIG. 2A) that is worn on the torso where the user's physical strength, stability, and tolerances are precisely monitored and measured Likened unto the wristband 110a, the vest 120a may include the system 200 as indicated in FIGS. 1 and 2A. One or more sensors 122 (240) may be embedded with the vest 120a as shown. In particular, these sensors 122 can represent one or more of the various types of sensors, IMU 242, thermistor 243, optical heart sensor 244, pulse oximeter (blood oxygen sensor) 245, heart monitor (deep learning) 246, and non-invasive glucose monitor 247. The system 200 within the ring 111 can include one or more of the various communication utilities: Bluetooth 260, Wi-Fi 262, NFC 264, RFID 266, and GSM 268. Further, the system 200 within the vest 120a can exchange information with other client devices 105. Another version of the vest 120c as shown in FIG. 4F, may include embedded one or more of the sensors as shown in FIG. 2A.

Figure 4G:
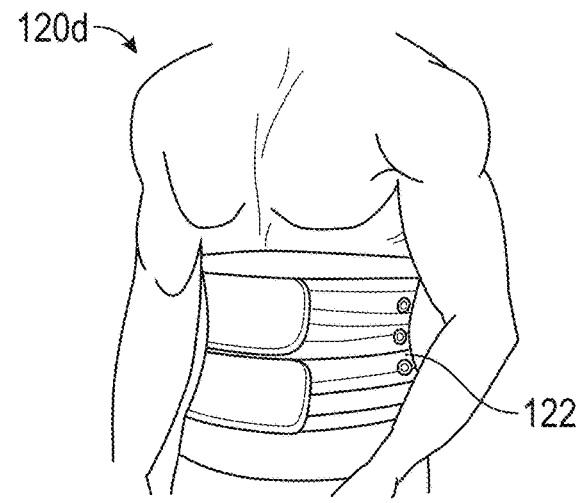
FIG. 4G is a perspective view of the waistband 120d of the exemplary network of FIG. 1, in accordance with some embodiments.

Referring now to FIG. 4G, a perspective view of the waistband 120d of the exemplary network of FIG. 1, in accordance with some embodiments is displayed. The waistband 120d may include a wearable monitoring device (including system 200 of FIG. 2A) that is worn on the torso where the user's physical strength, stability, and tolerances are precisely monitored and measured. The sensors 240 may be embedded within the waistband 120b as shown. In particular, various types of sensors, IMU 242, thermistor 243, optical heart sensor 244, pulse oximeter (blood oxygen sensor) 245, heart monitor (deep learning) 246, and non-invasive glucose monitor 247. The system 200 within the waistband 120b can include one or more of the various communication utilities: Bluetooth 260, Wi-Fi 262, NFC 264, RFID 266, and GSM 268. Further, the system 200 within the waistband 120b can exchange information with other client devices 105.

Referring now to FIG. 5A, an exemplary flow diagram of a method for dynamic biometric detection and response, in accordance with some embodiments is shown. In an action 505, the method may include initializing a safety protocol. For example, a safety policy for a senior, a diabetic, a heart disease patient, an Alzheimer's patient, a person with Attention Deficit Disorder (ADD), and the like may be selected by the user or the physician. Additionally, in an action 510, the method may include initializing a network security protocol for the purpose of protecting the privacy of each user's medical records. Further, in an action 515 the method may include retrieving a user profile from a storage unit. For example, a processor in concert with the medical detection agent may access a local or remote database to retrieve the user profile. The method may also include identifying user location in an action 520. In particular, the data processing method may include the step of sensing one or more satellite signals within the Global Positioning System (GPS), to detect the travel time of the signal; to calculate the distance between the processor and at least one satellite; and to calculate the user location based upon this distance. In an action 525, the method may include sensing user motion. For example, sensing user motion may occur by retrieval of at least one of the user's specific force, angular rate, or orientation from an Inertial Measurement Unit (IMU). In an action 530, the method may further include detecting user activity based upon the sensed user motion, the detected location, and the user profile. For example, the method may include a data processing step of parsing the user profile to identify a predetermined set of locations and associated activities, wherein each activity having a corresponding motion. From a comparison of the detected location with the predetermined set of locations, the method may include comparing the sensed user motion with the corresponding motion of the matched location. Further in an action 535, the method may include sensing the biomarkers of the user and detecting the user's behavior pattern. For example, the method may include the step of retrieving the user's temperature from a thermometer; retrieving the user's blood pressure from a sensing unit having a deep learning algorithm associated with monitoring heart rate; retrieving the user's blood oxygen level from a pulse oximeter blood oxygen sensor; retrieving the user's blood glucose level from a non-invasive glucose monitor; and retrieving the user's pulse from an optical heart sensor. Further, the method may include detecting the user's behavior pattern in an action 540. For example, the method may include monitoring the user action using advanced machine-learning algorithms, including principal component analysis and neural network computations; and identifying repetitive actions to indicate the detected user behavior pattern (to be described further in detail with reference to FIG. 5B). Moreover, the method may include detecting an anomaly based upon the detected user's behavior pattern, the sensed biomarkers, the user activity, and the user profile in an action 555; and generating an anomaly alert for third party notification and quantitative analysis at a server in an action 560-580. In particular, the method may generate a record of the detected anomaly in an action 560. Further, the method may include updating the user profile with the generated record in an action 565. The method may include generating an anomaly report based upon the detected anomaly in an action 570. Additionally, the method may include sending the anomaly report to a third party in an action 575 and sending the anomaly report of a network server in an action 580.

Referring now to FIG. 5B, an exemplary flow diagram of a method for monitoring user activity using an enhanced machine-learning algorithm to identify repetitive actions in user behavior pattern of FIG. 5A (step 540) in accordance with some embodiments is shown. In particular, the user data may be retrieved in an action 542. Next a master matrix may be formed in an action 544. As described with reference to FIG. 3, there are three routes (Route 1, Route 2, or the Enhanced Route AB) that the data can take in order to be processed. In particular, the switches S1-S4 can be set to enable a first mode through Route 1; a second mode through Route 2; and third mode through the Enhanced Route AB. During the first route (Route 1), one or more abridged matrices may be generated using the master matrix in an action 546. Next in an action 554, the one or more matrices can be processed using one or more pattern recognition techniques [e.g. Principal Component Analysis (PCA), Linear Discriminant Analysis (LDA)].

In some embodiments, the method may be set to process the data using Route 2, wherein the data is processed using a Convolution Neural Network (CNN) as indicated in action 550. In other embodiment, the method may be set to process the matrix using the Enhanced Route AB, wherein one abridged matrix can be extracted from the set of one or more abridged matrices in an action 548. This one abridged matrix can be sent to be process using CNN in the action 550. Further, a matrix can be extracted from the CNN processed matrix that includes a set of features and relative weight factors in an action 552. In the action 554, the extracted matrix can be processed using one or more pattern recognition techniques [e.g. Principal Component Analysis (PCA), Linear Discriminant Analysis (LDA)]. Accordingly, the Enhanced Route AB of processing the data can generate an optimum result, having precision, and speed, without the excessive use of computing resources.

It should be appreciated that the methods described herein may be performed with a digital processing system, such as a conventional, general-purpose computer system. Special purpose computers, which are designed or programmed to perform only one function may be used in the alternative. FIG. 6 is an illustration showing an exemplary computing device, which may implement the embodiments described herein. The computing device of FIG. 6 may be used to perform embodiments of the functionality for performing the dynamic biometric detection and response in accordance with some embodiments (as outlined in FIGS. 2A, 2B, 5A and 5B). The computing device includes a central processing unit (CPU) 602, which is coupled through a bus 606 to a memory 604, and mass storage device 608. Mass storage device 608 represents a persistent data storage device such as a floppy disc drive or a fixed disc drive, which may be local or remote in some embodiments. The mass storage device 608 could implement a backup storage, in some embodiments. Memory 604 may include read only memory, random access memory, and the like. Applications resident on the computing device may be stored on or accessed through a computer readable medium such as memory 604 or mass storage device 608 in some embodiments. Applications may also be in the form of modulated electronic signals modulated accessed through a network modem or other network interface of the computing device. It should be appreciated that CPU 602 may be embodied in a general-purpose processor, a special purpose processor, or a specially programmed logic device in some embodiments.

Display 612 is in communication with CPU 602, memory 604, and mass storage device 608, through bus 606. Display 612 is configured to display any visualization tools or reports associated with the system described herein. Input/output device 610 is coupled to bus 606 in order to communicate information in command selections to CPU 602. It should be appreciated that data to and from external devices may be communicated through the input/output device 610. CPU 602 can be defined to execute the functionality described herein to enable the functionality described with reference to FIGS. 1-5B. The code embodying this functionality may be stored within memory 604 or mass storage device 608 for execution by a processor such as CPU 602 in some embodiments. The operating system on the computing device may be iOS™, MS-WINDOWS™, OS/2™, UNIX™, LINUX™, or other known operating systems. It should be appreciated that the embodiments described herein may be integrated with virtualized computing system also.

The embodiments can also be embodied as computer readable code on a non-transitory computer readable medium. The computer readable medium is any data storage device that can store data, which can be thereafter read by a computer system. Examples of the computer readable medium include hard drives, network attached storage (NAS), read-only memory, random-access memory, CD-ROMs, CD-Rs, CD-RWs, magnetic tapes, flash memory devices, and other optical and non-optical data storage devices. The computer readable medium can also be distributed over a network coupled computer system so that the computer readable code is stored and executed in a distributed fashion. Embodiments described herein may be practiced with various computer system configurations including hand-held devices, tablets, microprocessor systems, microprocessor-based or programmable consumer electronics, minicomputers, mainframe computers and the like. The embodiments can also be practiced in distributed computing environments where tasks are performed by remote processing devices that are linked through a wire-based or wireless network.

In various embodiments, one or more portions of the methods and mechanisms described herein may form part of a cloud-computing environment. In such embodiments, resources may be provided over the Internet as services according to one or more various models. Such models may include Infrastructure as a Service (IaaS), Platform as a Service (PaaS), and Software as a Service (SaaS). In IaaS, computer infrastructure is delivered as a service. In such a case, the computing equipment is generally owned and operated by the service provider. In the PaaS model, software tools and underlying equipment used by developers to develop software solutions may be provided as a service and hosted by the service provider. SaaS typically includes a service provider licensing software as a service on demand. The service provider may host the software, or may deploy the software to a customer for a given period of time. Numerous combinations of the above models are possible and are contemplated.

In the above description, numerous details are set forth. It will be apparent, however, to one skilled in the art, that the present invention may be practiced without these specific details. In some instances, well-known structures and devices are shown in block diagram form, rather than in detail, in order to avoid obscuring the present invention.

It is to be understood that the above description is intended to be illustrative, and not restrictive. Many other embodiments will be apparent to those of skill in the art upon reading and understanding the above description. Although the present invention has been described with reference to specific exemplary embodiments, it will be recognized that the invention is not limited to the embodiments described, but can be practiced with modification and alteration within the spirit and scope of the appended claims. Specific functional details disclosed herein are merely representative for purposes of describing embodiments. Embodiments may, however, be embodied in many alternate forms and should not be construed as limited to only the embodiments set forth herein. Accordingly, the specification and drawings are to be regarded in an illustrative sense rather than a restrictive sense. The scope of the invention should, therefore, be determined with reference to the appended claims, along with the full scope of equivalents to which such claims are entitled.

Although the method operations were described in a specific order, it should be understood that other operations may be performed in between described operations, described operations may be adjusted so that they occur at slightly different times or the described operations may be distributed in a system which allows the occurrence of the processing operations at various intervals associated with the processing.

It should be understood that although the terms first, second, etc. may be used herein to describe various steps or calculations, these steps or calculations should not be limited by these terms. These terms are only used to distinguish one step or calculation from another. For example, a first calculation could be termed a second calculation, and, similarly, a second step could be termed a first step, without departing from the scope of this disclosure. As used herein, the term "and/or" and the "/" symbol includes any and all combinations of one or more of the associated listed items. As used herein, the singular forms "a", "an" and "the" are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. Therefore, the terminology used herein is for the purpose of describing particular embodiments only and is not intended to be limiting.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved. With the above embodiments in mind, it should be understood that the embodiments might employ various computer-implemented operations involving data stored in computer systems. These operations are those requiring physical manipulation of physical quantities. Usually, though not necessarily, these quantities take the form of electrical or magnetic signals capable of being stored, transferred, combined, compared, and otherwise manipulated. Further, the manipulations performed are often referred to in terms, such as producing, identifying, determining, or comparing. Any of the operations described herein that form part of the embodiments are useful machine operations. The embodiments also relate to a device or an apparatus for performing these operations. The apparatus can be specially constructed for the required purpose, or the apparatus can be a general-purpose computer selectively activated or configured by a computer program stored in the computer. In particular, various general-purpose machines can be used with computer programs written in accordance with the teachings herein, or it may be more convenient to construct a more specialized apparatus to perform the required operations.

A module, an application, a layer, an agent or other method-operable entity could be implemented as hardware, firmware, or a processor executing software, or combinations thereof. It should be appreciated that, where a software-based embodiment is disclosed herein, the software can be embodied in a physical machine such as a controller. For example, a controller could include a first module and a second module. A controller could be configured to perform various actions, e.g., of a method, an application, a layer or an agent.

What is claimed is:

1. A method of data processing for a dynamic biometric detection system, having by a processor-based medical detection agent, comprising:
    retrieving a user profile associated with a user from a storage unit by the processor-based medical detection agent;
    training the dynamic biometric detection system over a predetermined time period to form a behavior model associated with the user, wherein the training comprises,
        detecting user location associated with the user, using an GPS device within a user behavior module of the processor-based medical detection agent;
        sensing user motion associated with the user, using a plurality of sensors coupled to the processor-based medical detection agent;
        detecting user activity based upon the sensed user motion, the detected location, and the user profile using an activity detection unit within the user behavior module;
        sensing biomarkers of the user, using the processor-based medical detection agent;
        detecting user behavior pattern to form the behavior model associated with the user over the training predetermined time period, using a user behavior module within the processor-based medical detection agent, wherein detecting user behavior pattern comprises,
            generating a master matrix of sensed biomarkers, detected user location, sensed user motion, and detected user activity associated with the user,
            extracting a set of one or more abridged matrices from the master matrix,
            selecting a first matrix from the extracted set,
            processing the first matrix using a Convolution Neural Network (CNN),
            extracting a second matrix from the CNN processed matrix, and
            generating the user behavior pattern from the extracted second matrix using a pattern recognition technique to identify repetitive data inputs associated with the user profile to form the behavior model;
    detecting one or more parameters continuously from the group consisting of user location, user motion, user activity, and biomarkers;
    determining an anomaly based upon the behavior model associated with the user and the detected one or more parameters, using an operations module and a policy manager within the processor-based medical detection agent;
    generating a record of the detected anomaly, using an alert generator within the processor-based medical detection agent; and
    updating the user profile with the generated record using the processor-based medical detection agent.

2. The method of claim 1, wherein detecting of user location comprises,
    sensing one or more satellite signals within a Global Positioning System (GPS);
    detecting travel time of a signal by subtracting a time of receipt from a time of broadcast;
    calculating distance between the processor and at least one satellite associated with the one or more satellite signals, based upon the detected travel time multiplied by speed of light;

calculating the user location based upon the distance; and
updating user profile.

3. The method of claim 1, wherein sensing of user motion comprises,
retrieving at least one of the user's specific force, angular rate, or orientation from an Inertial Measurement Unit (IMU); and
updating user profile.

4. The method of claim 1, wherein detecting user activity comprise,
parsing the user profile to identify a predetermined set of locations, and associated activities, wherein each activity having a corresponding motion;
comparing the detected location with the predetermined set of locations;
comparing, in response to a matched location, the sensed user motion with the corresponding motion of the matched location;
setting, in response to a motion match, the associated activity of the corresponding motion to be the detected user activity; and
updating user profile.

5. The method of claim 1, wherein sensing biomarkers of the user comprises,
retrieving the user's temperature from a thermistor;
retrieving the user's blood pressure from a heart rate sensing unit having a deep learning algorithm;
retrieving the user's blood oxygen level from a pulse oximeter blood oxygen sensor;
retrieving the user's pulse from an optical heart sensor;
retrieving the user's blood glucose levels from a non-invasive glucose monitor; and
updating user profile with the user temperature, blood pressure, blood oxygen level, and pulse.

6. The method of claim 1, wherein the pattern recognition technique comprises Principal Component Analysis (PCA).

7. The method of claim 1, wherein the pattern recognition technique comprises Linear Discriminate Analysis (LDA).

8. The method of claim 1, wherein detecting the anomaly comprises,
retrieving the detected user behavior pattern, the sensed biomarkers, user activity, and the user profile;
parsing the user profile to identify a stored user behavior pattern;
comparing the user activity with the detected user behavior pattern and the stored user behavior pattern;
generating, in response to an absence of a match, an anomaly alert; and
updating user profile with the anomaly alert.

9. The method of claim 8, further comprises,
generating an anomaly report based upon the anomaly alert;
sending the anomaly report to a third party;
sending the anomaly report to a network server; and
generating a qualitative data report based upon user profile.

10. The method of claim 1, further comprises,
triggering Radio-Frequency IDentification (RFID) of a pill bottle;
retrieving pill prescription data; and
updating user profile.

11. The method of claim 1, further comprises,
triggering Near-Field Communication (NFC) unit of a pill dispenser;
retrieving pill dispenser data; and
updating user profile.

12. A dynamic biometric monitoring network system having by a processor-based medical detection agent, comprising:
a memory; and
a processor-based medical detection agent, having a processor coupled to the memory, the processor operable to:
initialize a safety protocol;
initialize a network security protocol;
retrieve a user profile associated with a user from a storage unit;
training the dynamic biometric detection system over a predetermined time period to form a behavior model associated with the user, wherein the training comprises:
identify user location associated with the user;
sense user motion associated with the user;
detect user activity based upon the sensed user motion, the detected location, and the user profile;
sense biomarkers of the user;
detecting user behavior pattern using a machine learning algorithm to form the behavior model associated with the user over the training predetermined time period, wherein detecting user behavior pattern comprises:
generate a master matrix of sensed biomarkers, user location, and user activity;
extract a set of one or more abridged matrices from the master matrix;
select a first matrix from the extracted set;
process the first matrix using a Convolution Neural Network (CNN);
extract a second matrix from the CNN processed matrix; and
detect a change and difference between an existing model and a new routine/behavior using a pattern recognition technique and identify repetitive actions to indicate the detected user behavior pattern to form the behavior model,
detect an anomaly based upon the formed behavior model and the detected user behavior pattern, the sensed biomarkers, user activity, and the user profile;
generate a record of the detected anomaly; and
update the user profile with the generated record.

13. The dynamic biometric monitoring network system of claim 12, further comprising:
generating an anomaly report based upon the detected anomaly;
sending the anomaly report to a third party;
sending the anomaly report to a network server; and
generating a qualitative data report based upon user profile.

14. The dynamic biometric monitoring network system of claim 12, wherein the processor, for the detecting the change and difference between the existing model and new routine/behavior operable to: use Principal Component Analysis (PCA) to process the second matrix.

15. A non-transitory computer-readable medium including code for performing a method of data processing for a dynamic biometric detection system having by a processor-based medical detection agent, the method comprising:
initializing a safety protocol using a policy manager within the processor-based medical detection agent;
initializing a network security protocol using the policy manager;

retrieving a user profile associated with a user from a storage unit by the processor-based medical detection agent;

training the dynamic biometric detection system over a predetermined time period to form a behavior model associated with the user, wherein the training comprises, detecting user location associated with the user, using an GPS device within a user behavior module of the processor-based medical detection agent, sensing user motion associated with the user, using a plurality of sensors coupled to the processor-based medical detection agent, detecting user activity based upon the sensed user motion, the detected location, and the user profile using an activity detection unit within the user behavior module, sensing biomarkers of the user, using the processor-based medical detection agent, and detecting user behavior pattern to form the behavior model associated with the user over the training predetermined time period, using a user behavior module within the processor-based medical detection agent, wherein detecting user behavior pattern comprises, generating a master matrix of sensed biomarkers, detected user location, sensed user motion, and detected user activity associated with the user, extracting a set of one or more abridged matrices from the master matrix, selecting a first matrix from the extracted set, processing the first matrix using a Convolution Neural Network (CNN), extracting a second matrix from the CNN processed matrix, and generating the user behavior pattern from the extracted second matrix using a pattern recognition technique to identify repetitive data inputs associated with the user profile to form the behavior model;

detecting one or more parameters continuously from the group consisting of user location, user motion, user activity, and biomarkers;

determining an anomaly based upon the behavior model associated with the user and the detected one or more parameters, using an operations module and a policy manager within the processor-based medical detection agent;

generating a record of the detected anomaly, using an alert generator within the processor-based medical detection agent; and updating the user profile with the generated record using the processor-based medical detection agent.

16. The computer-readable medium of claim 15, wherein the pattern recognition technique comprises Principal Component Analysis (PCA).

* * * * *